(12) United States Patent
Senetar

(10) Patent No.: US 9,809,512 B2
(45) Date of Patent: Nov. 7, 2017

(54) ADSORPTIVE RECOVERY OF BUTADIENE FROM ON PURPOSE BUTADIENE PRODUCTION

(71) Applicant: UOP LLC, Des Plaines, IL (US)

(72) Inventor: John J. Senetar, Naperville, IL (US)

(73) Assignee: UOP LLP, Des Plaines, IL (US)

( * ) Notice: Subject to any disclaimer, the term of this patent is extended or adjusted under 35 U.S.C. 154(b) by 149 days.

(21) Appl. No.: 14/556,893

(22) Filed: Dec. 1, 2014

(65) Prior Publication Data

US 2016/0152529 A1 Jun. 2, 2016

(51) Int. Cl.
| | |
|---|---|
| C07C 7/12 | (2006.01) |
| C07C 7/13 | (2006.01) |
| C07C 5/327 | (2006.01) |
| C07C 5/48 | (2006.01) |
| C07C 7/11 | (2006.01) |

(52) U.S. Cl.
CPC .............. *C07C 5/48* (2013.01); *C07C 5/327* (2013.01); *C07C 7/11* (2013.01)

(58) Field of Classification Search
CPC .............. C07C 7/12; C07C 7/13; C07C 5/327
USPC ................ 585/820, 825, 826, 829, 616, 621
See application file for complete search history.

(56) References Cited

U.S. PATENT DOCUMENTS 3,992,471 A * 11/1976 Priegnitz .................. C07C 7/13
585/829
4,595,788 A * 6/1986 Yamamoto ............ C07C 11/167
585/621

* cited by examiner

*Primary Examiner* — Thuan D Dang

(57) ABSTRACT

A process is presented for the production of butadienes. The process includes the recovery of a crude butadiene stream using adsorption separation and removes the need to compress the effluent stream from the oxidative dehydrogenation process effluent stream. The process includes an adsorption step to remove C4 compounds from the oxidative effluent stream, a desorption step to recover the adsorbed C4 compounds and a regeneration step to regenerate the adsorbent for continued use in the separation process.

8 Claims, 2 Drawing Sheets

ADSORPTIVE RECOVERY OF BUTADIENE FROM ON PURPOSE BUTADIENE PRODUCTION

FIELD OF THE INVENTION

The present invention relates to a process for the production of butadiene. In particular, this is a process for the integration of a butadiene recovery process in an oxidative dehydrogenation process.

BACKGROUND

The use of plastics and rubbers are widespread in today's world. The production of these plastics and rubbers are from the polymerization of monomers which are generally produced from petroleum. The monomers are generated by the breakdown of larger molecules to smaller molecules which can be modified. The monomers are then reacted to generate larger molecules comprising chains of the monomers. An important example of these monomers is light olefins, including ethylene and propylene, which represent a large portion of the worldwide demand in the petrochemical industry. Light olefins, and other monomers, are used in the production of numerous chemical products via polymerization, oligomerization, alkylation and other well-known chemical reactions. Producing large quantities of light olefin material in an economical manner, therefore, is a focus in the petrochemical industry. These monomers are essential building blocks for the modern petrochemical and chemical industries. The main source for these materials in present day refining is the steam cracking of petroleum feeds.

Another important monomer is butadiene. Butadiene is a basic chemical component for the production of a range of synthetic rubbers and polymers, as well as the production of precursor chemicals for the production of other polymers. Examples include homopolymerized products such as polybutadiene rubber (PBR), or copolymerized butadiene with other monomers, such as styrene and acrylonitrile. Butadiene is also used in the production of resins such as acrylonitrile butadiene styrene.

Butadiene is typically recovered as a byproduct from the cracking process, wherein the cracking process produces light olefins such as ethylene and propylene. With the increase in demand for rubbers and polymers having the desired properties of these rubbers, an aim to improving butadiene yields from materials in a petrochemical plant will improve the plant economics. The economics of butadiene production can be strongly affected by capital and operating costs.

SUMMARY

The present invention provides a process for butadiene production and recovery with the removal of expensive equipment and a reduction in operating costs.

A first embodiment of the invention is a process for the production of butadienes comprising passing a butene stream and an oxidative stream comprising oxygen to an oxidative dehydrogenation reactor to generate a process stream comprising C4s; passing the process stream to an adsorptive separation unit, comprising an adsorber, to generate a first stream with a reduced C4 content and retaining the C4s in the adsorber; passing a solvent stream to the adsorptive separation unit to generate a second stream comprising C4s and solvent; passing the second stream to a solvent recovery unit to generate a third stream comprising C4s, and a fourth stream comprising solvent; and passing the third stream to a butadiene recovery unit to generate a product stream comprising butadienes. An embodiment of the invention is one, any or all of prior embodiments in this paragraph up through the first embodiment in this paragraph further comprising passing the process stream to a quench system before passing the process stream to the adsorptive separation unit, to generate a cooled process stream with reduced water content. An embodiment of the invention is one, any or all of prior embodiments in this paragraph up through the first embodiment in this paragraph further comprising passing the cooled process stream with reduced water content to a dryer to generate a dried cooled process stream; and passing the dried cooled process stream to the adsorptive separation system. An embodiment of the invention is one, any or all of prior embodiments in this paragraph up through the first embodiment in this paragraph further comprising passing a regenerant stream to the adsorptive separation unit after passing the solvent stream to the adsorptive separation unit, to generate an adsorbent depleted in solvent and a regenerant effluent stream comprising the regenerant gas and solvent. An embodiment of the invention is one, any or all of prior embodiments in this paragraph up through the first embodiment in this paragraph further comprising passing the regenerant effluent stream to a solvent recovery unit. An embodiment of the invention is one, any or all of prior embodiments in this paragraph up through the first embodiment in this paragraph wherein the regenerant stream comprises nitrogen. An embodiment of the invention is one, any or all of prior embodiments in this paragraph up through the first embodiment in this paragraph wherein the solvent recovery comprises passing the regenerant effluent stream to a condensing unit to condense the solvent from the regenerant effluent stream and to generate a recovered solvent stream. An embodiment of the invention is one, any or all of prior embodiments in this paragraph up through the first embodiment in this paragraph wherein the solvent is selected from the group consisting of acetonitrile, N-methylpyrrolidone, furfural, dimethylformamide, C5+ hydrocarbons, oxygenates with boiling points higher than butadiene, compounds that selectively extract butenes and butadiene from hydrocarbon mixtures, and mixtures thereof.

A second embodiment of the invention is a process for the production of butadienes comprising passing a butane stream to a dehydrogenation reactor to generate a stream comprising butenes; passing the stream comprising butenes to an oxidative dehydrogenation reactor to generate a stream comprising butadienes and other C4 hydrocarbons; passing the stream comprising butadienes to an adsorption unit to generate a first stream having reduced C4 content; passing a solvent stream to the adsorption unit to generate a second stream comprising solvent and C4 hydrocarbons; and passing the second stream to a fractionation column to generate an overhead stream comprising C4 compounds and a bottoms stream comprising solvent. An embodiment of the invention is one, any or all of prior embodiments in this paragraph up through the second embodiment in this paragraph further comprising passing the overhead stream to butadiene separation unit to generate a butadiene process stream. An embodiment of the invention is one, any or all of prior embodiments in this paragraph up through the second embodiment in this paragraph further comprising passing a stream comprising hydrogen to the dehydrogenation reactor. An embodiment of the invention is one, any or all of prior embodiments in this paragraph up through the second embodiment in this paragraph comprising passing steam and air to the oxidative dehydrogenation reactor. An embodiment of the invention is one, any or all of prior embodiments in this paragraph up through the second embodiment in this paragraph further comprising passing a regenerant stream to the adsorption unit to generate a regenerant effluent stream comprising regenerant and solvent. An embodiment of the invention is one, any or all of prior embodiments in this paragraph up through the second embodiment in this paragraph further comprising passing the regenerant effluent stream to a solvent recovery unit.

A third embodiment of the invention is a process for the production of butadienes comprising passing a first stream comprising butenes to an oxidative dehydrogenation reactor; passing a compressed air stream to the oxidative dehydrogenation reactor; passing a steam stream to the dehydrogenation reactor, wherein an effluent stream comprising butadienes is generated; passing the effluent stream to a quench system to generate a cooled effluent stream and a water stream; passing the cooled effluent to a drier to generate a dried cooled stream; passing the dried cooled stream to an adsorber, comprising an adsorbent, to generate an effluent stream comprising light gases, and to adsorb the C4 compounds on the adsorbent; passing a solvent stream to the adsorber to generate an desorption stream comprising solvent and C4 compounds; passing the desorption stream to a solvent recovery column to generate a bottoms stream comprising solvent and an overhead stream comprising C4 compounds. An embodiment of the invention is one, any or all of prior embodiments in this paragraph up through the third embodiment in this paragraph further comprising passing the overhead stream to a butadiene separation unit to generate a butadiene product stream and a raffinate stream comprising butenes and butane. An embodiment of the invention is one, any or all of prior embodiments in this paragraph up through the third embodiment in this paragraph further comprising passing the water stream to a treatment unit to generate a treated water stream. An embodiment of the invention is one, any or all of prior embodiments in this paragraph up through the third embodiment in this paragraph further comprising passing the treated water stream to a heat exchanger to generate a stream comprising steam. An embodiment of the invention is one, any or all of prior embodiments in this paragraph up through the third embodiment in this paragraph further comprising passing a regenerant stream to the adsorber after passing the solvent stream to the adsorber, to generate an adsorbent depleted in solvent and a regenerant effluent stream comprising the regenerant gas and solvent. An embodiment of the invention is one, any or all of prior embodiments in this paragraph up through the third embodiment in this paragraph further comprising passing the regenerant effluent stream to a solvent recovery unit.

Other objects, advantages and applications of the present invention will become apparent to those skilled in the art from the following detailed description and drawings.

DETAILED DESCRIPTION

With a decrease in the recovery of butadienes from naphtha cracking, on purpose butadiene production has been developed. Currently, one of the more economically viable means of on purpose butadiene production is performed through the oxidative dehydrogenation of butenes. The process operates at low pressure using air to supply the oxygen and stream for added dilution. The combination of the nitrogen in the air and the dilution steam results in a dilute intermediate product stream and thus requires substantial downstream processing for butadiene recovery. The process involves compressing the dilute intermediate product stream. The compression includes an expensive compressor that is a substantial portion of the capital cost, or upwards of about 40% of the capital cost. In addition, the utilities for operating a compressor are substantial and account for a large portion of the operating cost.

Figure 1:
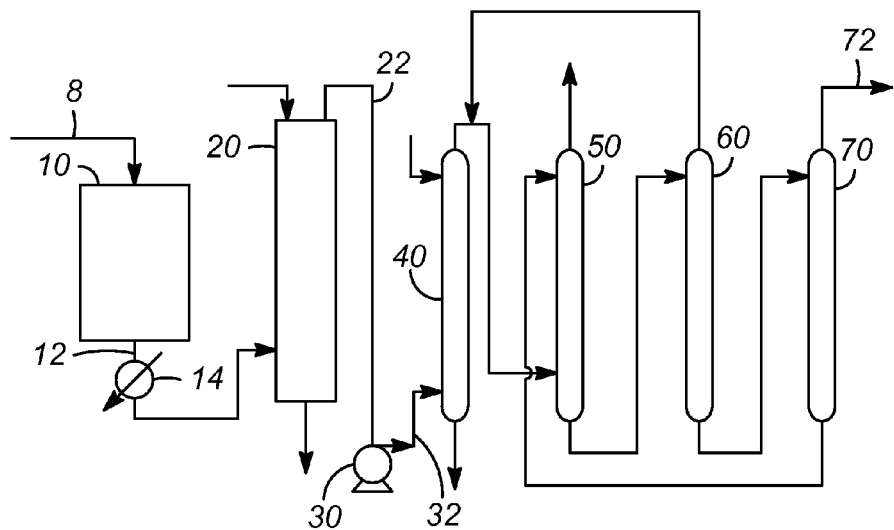
FIG. 1 is a diagram of an oxidative dehydrogenation process.

The process, as seen in FIG. 1, includes passing a feedstream comprising steam, air and butenes 8 to a oxidative dehydrogenation reactor 10. An intermediate product stream 12 having butadienes is cooled through a heat exchanger 14 and a quench tower 20, where a portion of the water is removed. A cooled and quenched stream 22 is passed to a compressor 30 to generate a compressed intermediate product stream 32. The compressed stream 32 is passed through a scrubbing tower 40, an adsorption tower 50, a degassing tower 60 and a stripping tower 70 to generate a crude butadiene stream 72 for further processing.

Figure 2:
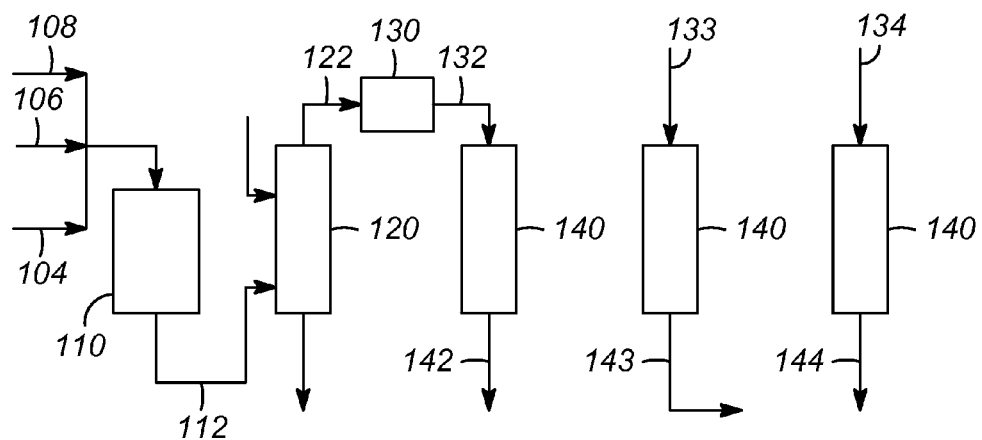
FIG. 2 is a diagram of the use of adsorptive recovery of C4s.

The present invention removes the compressor 30, and the need to compress the intermediate product stream. The process, as shown in FIG. 2, includes passing a butene stream 108, an oxygen laden stream 106 and steam 104 to an oxidative dehydrogenation reactor 110 to generate a process stream 112 comprising C4 compounds, including butadienes. The process stream 112 is passed to a quench unit 120 to remove water and to cool the process stream 122. The cooled process stream 122 is passed through a dryer 130 to further remove residual water from the process stream 132.

The cooled and dried process stream 132 is passed to an adsorption separation unit 140, comprising an adsorber to generate a first stream 142 with a reduced C4 content, and retaining the C4s in the adsorption separation unit 140. The adsorption separation unit 140 is then changed to desorption mode, and a solvent stream 133 is passed to the adsorption separation unit 140 to generate a second stream 143 comprising C4s and solvent. The second stream 143 is passed to a solvent recovery unit to generate a third stream comprising C4s and a fourth stream comprising solvent. The third stream is passed to a butadiene recovery unit to generate a product stream comprising butadienes.

The process can further include regenerating the adsorption separation unit 140. A regenerant stream 134 is passed to the adsorptive separation unit 140 to generate an adsorbent depleted in solvent and a regenerant effluent stream 144 comprising regenerant gas and solvent. The regenerant effluent gas is passed to a solvent recovery unit. The solvent recovery includes passing the regenerant stream to a condensing unit to condense the solvent, thereby separating the solvent from the regenerant gas, and generating a recovery solvent stream. The solvent is recycled to the adsorption separation unit during the desorption phase. The regenerant stream can comprise any gas that can displace the solvent. A preferred regenerant stream comprises nitrogen.

Solvents usable in the present process include acetonitrile, N-methylpyrrolidone, furfural, dimethylformamide, C5+ hydrocarbons, oxygenates with boiling points higher than butadiene, compounds that selectively extract butenes and butadiene from hydrocarbon mixtures. Mixtures of solvents from this list can also be used.

Figure 3:
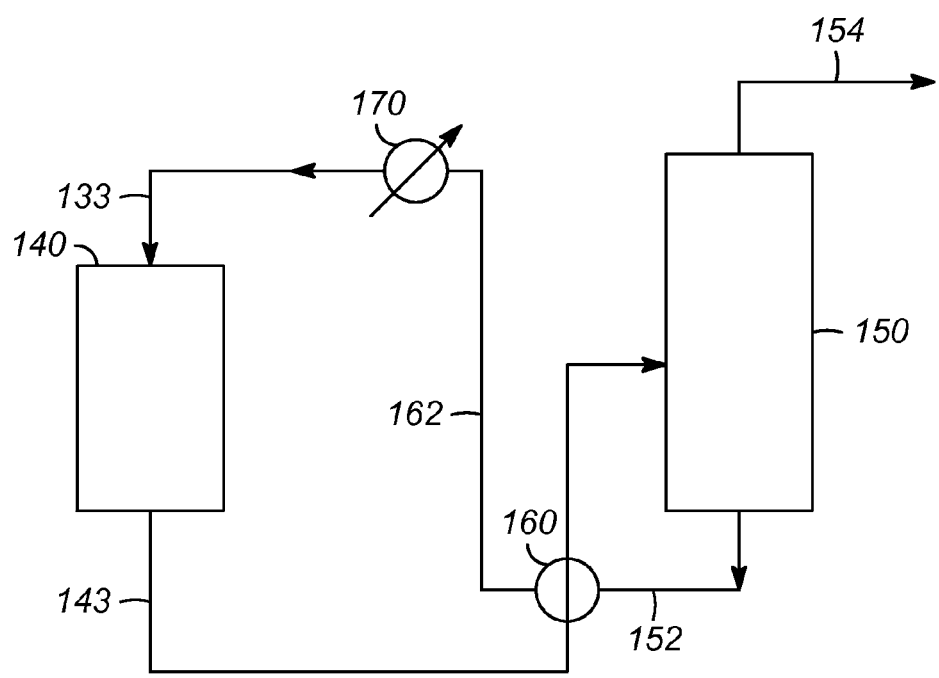
FIG. 3 is a diagram of the solvent recovery and generation of the C4 stream from the oxidative dehydrogenation process.

As shown in FIG. 3, the desorption step generates the second, or desorption, stream 143 comprising solvent and C4s. The desorption stream 143 is passed to a solvent stripper 150 to generate a bottoms stream 152 comprising solvent, and an overhead stream 154 comprising C4s. The overhead stream 154 is passed to a butadiene separation unit. The bottoms stream 152 can be heat exchanged with the desorption stream 143 through a feed heat exchanger 160. The heated solvent stream 162 can be further heated by a heater 170 to generate a the solvent stream 133 in a vapor state.

The use of an adsorption separation system rather than the compression and separation downstream can reduce both capital costs and operating costs. A benefit also includes a reduction in the fouling tendencies of the compressed stream containing butadienes.

In another embodiment, the process for the production of butadienes includes, passing a butane stream to a dehydrogenation reactor to generate a stream comprising butenes. The stream comprising butenes is passed to an oxidative dehydrogenation reactor to generate an effluent stream comprising butadienes and other C4 hydrocarbons. The stream comprising butadienes is passed to an adsorption unit, wherein the butadienes and other C4 compounds are adsorbed, thereby generating a first stream having a reduced C4 content. The process can include multiple adsorption columns, and comprises at least two. When a first adsorption column is sufficiently loaded with C4 compounds, the stream comprising butadienes is switched to a second adsorption column, and the first column is switched to a desorption mode. A solvent stream is passed to the first adsorption column in desorption mode to generate a second stream comprising solvent and C4 hydrocarbons. When the first adsorption column is sufficiently cleared of C4 hydrocarbons by desorption, the first adsorption column is switched to a regeneration mode. The second stream is passed to a fractionation column to generate an overhead stream comprising C4 compounds and a bottoms stream comprising solvent.

The process can further include passing the overhead stream to a butadiene separation unit to generate a butadiene process stream. The process can further include passing hydrogen to the dehydrogenation reactor, and passing steam and air to the oxidative dehydrogenation reactor.

When the first adsorption column is in regeneration mode, a regenerant stream is passed to the first adsorption column to generate a regenerant effluent stream comprising regenerant gas and solvent. The regenerant effluent stream is passed to a solvent recovery unit to separate the solvent from the regenerant effluent stream. Preferably the regenerant gas is a non-condensing gas, such as nitrogen, and the solvent recovery unit can comprise a condensing unit to condense the solvent from the regenerant effluent stream.

In another embodiment, the invention for the production of butadienes includes passing a first stream comprising butenes to an oxidative dehydrogenation reactor. The oxidative dehydrogenation reactor has a feedstream that includes stream and a source of oxygen. The oxygen is preferably supplied by an air supply. The reactor generates an effluent stream comprising butenes and butadienes. The effluent stream is quenched in a quench system to cool and remove water. The effluent stream also comprise light gases such as nitrogen, oxygen, carbon oxides, and light gas, such as hydrogen or methane. The cooled effluent stream is passed to a dryer to remove residual water from the effluent stream. The cooled and dried effluent stream is passed to an adsorber, wherein the adsorber has an adsorbent selected to adsorb C4 compounds, and in particular butadienes and butenes. The effluent from the adsorber comprises light gases with the C4 hydrocarbons removed. The adsorber is operated in parallel with at least one additional adsorber, with at least one adsorber on-line and another adsorber off-line. The on-line adsorber is switched to an off-line condition, and the cooled and dried effluent stream is switched to another adsorber when the on-line adsorber is taken off-line. The now taken off-line adsorber is changed to desorption mode. A solvent stream is passed to the now taken off-line adsorber to generate a desorption stream comprising solvent and C4 compounds. The desorption stream is passed to a solvent recovery unit to separate the desorption stream into an overhead stream comprising C4 compounds and a bottoms stream comprising solvent.

A further aspect of this embodiment includes passing the overhead stream to a butadiene separation unit. The separation unit generates a butadiene product stream and a raffinate stream comprising butenes and butane.

The water separated from the oxidative dehydrogenation effluent stream can be passed to a water treatment unit to generate a treated water stream. This water stream can be recycled for further use, including passing the treated water to a heat exchanger to generate steam.

The adsorber is further changed over to a third operation mode, wherein the adsorbent in the adsorber is regenerated. The regeneration comprises removing the solvent and other residual components from the adsorbent in the process of removing the C4 compounds. The regeneration mode includes passing a regenerant gas stream to the adsorber to remove solvent and to generate an adsorbent depleted in solvent and a regenerant effluent stream comprising regenerant gas and solvent. The regenerant gas is preferably a non-condensing gas such as nitrogen. The regenerant effluent stream is passed to an solvent recovery unit, wherein the solvent is condensed and recycled for use in regenerating an adsorber.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for the production of butadienes comprising:
passing a butene stream and an oxidative stream comprising light gasses including oxygen to an oxidative dehydrogenation reactor to generate a process stream comprising light gasses, unreacted oxygen and C4s including butenes and butadienes;
passing the process stream to an adsorptive separation unit, comprising an adsorber, to generate a first stream comprising the light gasses and unreacted oxygen and retaining the C4s including the butenes and butadienes in the adsorber;
passing a solvent stream to the adsorptive separation unit to generate a second stream comprising solvent and the $C_4$s including the butenes and butadienes;
passing the second stream to a solvent recovery unit to generate a third stream comprising $C_4$s including the butenes and butadienes, and a fourth stream comprising solvent; and
passing the third stream comprising $C_4$s including the butenes and butadienes to a butadiene recovery unit to generate a product stream comprising butadienes.

2. The process of claim 1 further comprising passing the process stream to a quench system before passing the process stream to the adsorptive separation unit, to generate a cooled process stream with reduced water content.

3. The process of claim 2 further comprising passing the cooled process stream with reduced water content to a dryer to generate a dried cooled process stream; and passing the dried cooled process stream to the adsorptive separation system.

4. The process of claim 1 further comprising passing a regenerant stream to the adsorptive separation unit after passing the solvent stream to the adsorptive separation unit, to generate an adsorbent depleted in solvent and a regenerant effluent stream comprising the regenerant gas and solvent.

5. The process of claim 4 further comprising passing the regenerant effluent stream to a solvent recovery unit.

6. The process of claim 4 wherein the regenerant stream comprises nitrogen.

7. The process of claim 5 wherein the solvent recovery comprises passing the regenerant effluent stream to a condensing unit to condense the solvent from the regenerant effluent stream and to generate a recovered solvent stream.

8. The process of claim 1 wherein the solvent is selected from the group consisting of acetonitrile, N-methylpyrrolidone, furfural, dimethylformamide, C5+ hydrocarbons, oxygenates with boiling points higher than butadiene, compounds that selectively extract butenes and butadiene from hydrocarbon mixtures, and mixtures thereof.

* * * * *